US007335367B2

(12) United States Patent
Borodic

(10) Patent No.: US 7,335,367 B2
(45) Date of Patent: Feb. 26, 2008

(54) TREATMENT OF CHRONIC CHALAZION AND HORDEOLUM WITH BOTULINUM TOXIN

(75) Inventor: Gary Borodic, Canton, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 0 days.

(21) Appl. No.: 10/793,739

(22) Filed: Mar. 8, 2004

(65) Prior Publication Data

US 2004/0175400 A1    Sep. 9, 2004

Related U.S. Application Data

(60) Provisional application No. 60/453,029, filed on Mar. 6, 2003.

(51) Int. Cl.
*A61K 39/08* (2006.01)
(52) U.S. Cl. .................. 424/239.1; 424/184.1
(58) Field of Classification Search ............ 424/236.1, 424/247.1, 183.1, 832, 239.1, 282.1, 434, 424/810, 78.02, 184.1; 530/350; 128/898; 514/2, 14
See application file for complete search history.

(56) References Cited

U.S. PATENT DOCUMENTS

| 5,401,243 | A | * | 3/1995 | Borodic ................ 604/511 |
| 5,670,484 | A | * | 9/1997 | Binder ................. 514/14 |
| 5,766,605 | A | * | 6/1998 | Sanders et al. ........ 424/239.1 |
| 6,063,768 | A | * | 5/2000 | First ................... 514/14 |
| 6,299,893 | B1 | * | 10/2001 | Schwartz et al. ........ 424/422 |
| 6,358,926 | B2 | * | 3/2002 | Donovan ............... 514/14 |
| 6,429,189 | B1 | * | 8/2002 | Borodic ............... 514/2 |
| 6,632,440 | B1 | * | 10/2003 | Quinn et al. .......... 424/239.1 |
| 2002/0082197 | A1 | | 6/2002 | Aoki et al. |
| 2003/0113349 | A1 | * | 6/2003 | Coleman, III ......... 424/239.1 |
| 2003/0157134 | A1 | * | 8/2003 | Aoki et al. .......... 424/239.1 |
| 2003/0180289 | A1 | * | 9/2003 | Foster et al. ......... 424/132.1 |
| 2004/0013692 | A1 | * | 1/2004 | Aoki et al. .......... 424/239.1 |
| 2004/0170665 | A1 | * | 9/2004 | Donovan .............. 424/427 |
| 2004/0226556 | A1 | * | 11/2004 | Deem et al. .......... 128/200.24 |
| 2004/0247606 | A1 | * | 12/2004 | Borodic et al. ....... 424/184.1 |
| 2005/0058666 | A1 | * | 3/2005 | Aoki et al. .......... 424/239.1 |
| 2005/0129716 | A1 | * | 6/2005 | Aoki et al. .......... 424/239.1 |
| 2005/0142105 | A1 | * | 6/2005 | Puri et al. ........... 424/85.2 |
| 2005/0147626 | A1 | * | 7/2005 | Blumenfeld .......... 424/239.1 |
| 2005/0220820 | A1 | * | 10/2005 | Sanders et al. ....... 424/239.1 |

FOREIGN PATENT DOCUMENTS

| EP | 1 005 867 A2 | 6/2000 |
| EP | 1 005 867 A3 | 6/2001 |
| WO | WO 95/28171 | 10/1995 |
| WO | WO 02/00172 A3 | 1/2002 |
| WO | 03/011333 | * 2/2003 |
| WO | WO 03/011333 A | 2/2003 |
| WO | 03/026602 | * 4/2003 |
| WO | 2004/016763 | * 2/2004 |
| WO | WO 2004/016763 A2 | 2/2004 |
| WO | WO 2004/016763 A3 | 2/2004 |

OTHER PUBLICATIONS

De Almeida, HL Jr. et al, International Journal of Dermatology, vol. 39, pp. 698-700, 2000.*
Heckmann, M et al, The New England Journal of Medicine, vol. 344(7), pp. 488-493, Feb. 15, 2001.*
Mauriello, JA Jr. et al, Br. J. Ophthalmol., Dec. 1996, vol. 80(12, pp. 1073-1076.*
Moguel-Ancheita, S et al, Arch. Soc. Esp. Oftalmol. 2003, vol. 78, pp. 9-14.*
O'Day, J, Curr. Opin. Ophthalmol. Dec. 2001, vol. 12(6), pp. 419-422, Use of botulinum toxin in neuro-ophthalmology.*
Sahlin, S et al, Am. J. Ophthalmol., Apr. 2000, vol. 129(4), pp. 481-486.*
Uddin, JM et al, Ophthalmology, Jun. 2002, vol. 109(6), pp. 1183-1187.*
Verheyden, J et al, Seminars in Cutaneous Medicine and Surgery, vol. 20(2), June, pp. 121-126.*
O'Day (2001) reference of record.*
Heckmann et al (2001) reference of record.*
Borodic et al "Botulinum toxin for the treatment of pain and inflammatory disorders," Expert Opin Investig 10(8) 1531-1544, 2001.
Carter, Susan R., Eyelid Disorders: Diagnosis and Management, XP-002286815.

* cited by examiner

Primary Examiner—Mark Navarro
Assistant Examiner—Ginny Allen Portner
(74) Attorney, Agent, or Firm—Milbank, Tweed, Hadley & McCloy, LLP

(57) ABSTRACT

Chalazia and hordeola are the most common lesions occurring in the human eyelid, and often recurrences are managed by surgical intervention to remove fatty inclusions within the lid with associated inflammatory reaction. The present invention provides non-surgical methods of treating chalazia, hordeola and cutaneous infections comprising the administration of compositions comprising botulinum toxin. The present invention provides methods that effectively block meibum secretion from the meibomian glands, reduce sebaceous bacterial culture media on skin, and sebaceous secretion from the glands of Zeis. Decreased production of meibum and associated fatty substances resulting from the methods of the present invention, decrease gland blockage and tissue inspissations, resulting in reduced recurrence of chalazia, hordeola and related inflammatory reactions and lesions.

25 Claims, No Drawings

TREATMENT OF CHRONIC CHALAZION AND HORDEOLUM WITH BOTULINUM TOXIN

This application claims benefit to U.S. Provisional Application Ser. No. 60/453,029 that was filed on Mar. 6, 2003.

TECHNICAL FIELD OF THE INVENTION

This invention relates to methods for treating disorders associated with abnormal secretion of meibomian and sebaceous secretions with botulinum toxin.

BACKGROUND OF THE INVENTION

Chalazion is a chronic granulomatous enlargement of a meibomian gland of the eyelid. This disorder is characterized by hypersecretion of meibum from the meibomian glands. This hypersecretion leads to an accumulation of fatty materials that form lesions that occlude the ductal elements of the gland, leading to an encroachment of the occlusion into the surrounding tissue, which further induces an inflammatory response. Similarly, hordeola is characterized by hypersecretion of sebum from sebaceous glands. Individuals suffering from Chalazia and/or hordeola are often treated by warm compresses or lid soaps which mechanically remove the excess secretion. This approach is often ineffective. The use of antibacterial eyedrops are occasionally effective, but rarely cure the underlying problem—hypersecretion of the meibomian and sebaceous glands that causes inflammation. Patients usually undergo multiple surgical procedures to remove fatty secretions and associated inflammatory cells within the glands to effect relief. Such procedures are painful and occasionally result in lid scarring and misdirection of the eyelashes. The present invention, however, provides an improved method of treating subjects suffering from Chalazion, hordeola and cutaneous infections, comprising the administration of botulinum toxin to reduce or prevent the secretion of meibum and sebum from meibomian and sebaceous glands, respectively.

Botulinum neurotoxin, a toxin isolated from a strain of *Clostridium botulinum*, a deadly toxin at higher concentrations and quantities, has been used as a valuable therapeutic for the treatment of many neuromuscular diseases (e.g., dystonia, hemifacial spasm, bruxism, spasticity, cerebral palsy, torticollis), as well as sensory disorders and cutaneous disorders (myofacial pain, migraine, tension headaches, neuropathy, hyperhydrosis). Although botulinum toxin has been used for the treatment of hyperhydrosis (sweating disorders) by presumably targeting the cholinergically-innervated eccrine sweat glands, the effects of botulinum toxin on other cutaneous glandular structures, such as the meibomian and sebaceous glands is undocumented and unappreciated. Both the consequences and pathology associated with hyperhydrosis and the aqueous secretate (sweat) of the eccrine glands are distinct and dramatically different than that associated with hypersecretion-disorders of the meibomian and sebaceous glands and their lipophilic secretions. Prior to the present invention, the utility of botulinum toxin to prevent recurring chalazion, hordeola, infection of the lipid-rich glandular secretions, and decrease these secretions has been unrecognized.

SUMMARY OF THE INVENTION

The present invention provides methods of treating chalazion in a subject in need thereof, comprising the step of administering a therapeutically effective amount of a composition comprising botulinum toxin to the subject, wherein the composition reduces secretion from the meibomian glands. In a preferred embodiment, the composition is administered by injection into the eyelid or conjunctiva at one or more injection sites.

The present invention also provides methods of treating hordeola in a subject in need thereof, comprising the step of administering a therapeutically effective amount of a composition comprising botulinum toxin to the subject, wherein the composition reduces secretion from the sebaceous glands. In a preferred embodiment, the composition is administered by injection into the eyelid or conjunctiva at one or more injection sites. Because meibum, the secretion from the meibomian gland, provide culture media for growth of pathologic bacteria such as *Staphylococcus aureus* and other mucosal and skin surface bacteria, decrease in its secretion has antibacterial effects.

The present invention also provides methods of treating a bacterial or fungal cutaneous infection in a subject in need thereof, comprising the step of administering a therapeutically effective amount of a composition comprising botulinum toxin to the subject, wherein the composition reduces cutaneous bacterial or fungal growth. In one embodiment, the infection is caused by an organism selected from the group consisting of: *Staphylococcus; Streptococcus* and *Moraxella*. Preferably, the methods of the present invention treat bacterial of fungal cutaneous infections in the eyelid, scalp, feet, groin, and armpit.

The present invention also provides methods of reducing a sebaceous or mucous secretion on a body surface in a subject in need thereof, comprising the step of administering a therapeutically effective amount of a composition comprising botulinum toxin to the subject, wherein the composition reduces sebaceous or mucous secretion.

The methods of the present invention may be practiced with various botulinum toxin immunotypes. In one embodiment, the botulinum toxin is any one or more botulinum toxin immunotypes selected from the group consisting of: A; B; C; D; E; F; and G. Furthermore, the methods of the present invention may utilize compositions of botulinum toxin wherein the composition is administered at a dose between 0.5 and 50,000 mouse $LD_{50}$ units of botulinum toxin.

The present invention further provides compositions comprising a botulinum toxin and a sequestration agent, wherein the sequestration agent is an albumin, preferably human serum albumin. Furthermore, in one embodiment, the albumin of the present compositions is recombinantly produced. In one embodiment, the albumin is present in an amount between 550 and 5,500 μg albumin per 100 $LD_{50}$ units botulinum toxin. In a further embodiment, albumin is present in an amount between 5,500 and 13,000 μg albumin per 100 $LD_{50}$ units botulinum toxin. In a preferred embodiment, albumin is present in an amount between 13,000 and 50,500 μg albumin per 100 $LD_{50}$ units botulinum toxin. In a more preferred embodiment, albumin is present in an amount between 50,500 and 505,000 μg albumin per 100 $LD_{50}$ units botulinum toxin. In a most preferred embodiment, albumin is formulated as encapsulated microspheres in an amount between 50,500 and 90,500 μg albumin per 100 $LD_{50}$ units botulinum toxin.

DETAILED DESCRIPTION OF THE INVENTION

A. Definitions.

As used herein, "Botulinum toxin" means a protein toxin and its complexes isolated from strains of *Clostridium botulinum*, including various immunotypes such as A, B, C1, C2, C3, D, E, F and G.

As used herein, "a therapeutically effective amount" is an amount sufficient to produce a therapeutic response. An effective amount may be determined with dose escalation studies in open-labeled clinical trials or bin studies with blinded trials.

As used herein, "subject" means a mammal.

B. Eyelid Disorders.

Chalazia occurs as a chronic deep inflammation of the lid associated with the accumulation of lipid material within macrophages (epithelioid cells) surrounding meibomian glands within the tarsal plate of the eyelid. The inflammation is characterized as a granulomatous-type inflammation associated with lipid and cellular lesions within soft tissues. In the case of chalazia, the lesions are formed by the secretion of the meibomian glands, the glands which contribute to the outer layers of the tear film covering the ocular surface. Histological analysis of these lesions reveal clear regions representing the lipid material, surrounded by polymorphonuclear leukocytes, plasma cells, giant cells, and lymphocytes.

Hordeola presents a similar pathologic process, however, these lesions occur from occluded sebaceous glands at the extreme of the eyelid margin. The resulting occlusion and excess sebum produces an inflammatory reaction similar to that observed in chalazion.

Chalazion formation has been associated with hypersecretion of the lipid-rich meibum from the meibomian gland. Alterations in the lipid composition of meibomian secretions, including free fatty acid and cholesterol content, have also been linked to Chalazion, producing tear film instability, irritation of conjunctival and corneal epithelium, and increased susceptibility to bacterial and fungal infections. Although numerous organism have been identified in the infections frequently associated with Chalazion, the most common isolated bacteria from blepharitic eyelids include species of *Staphylococcus, Corynebacterium*, and *Propionibacterium. Staphylococcus aureus* has been thought to flourish on hypersecretion of meibomian and related eyelid glands. In summary, the pathophysiology of chalazia and hordeola involves: 1) altered meibomian secretion and hypersecretion; 2) inflammation from secretion backup into soft tissue of the lid; and 3) secondary inflammation.

The methods of the present invention may also be used to treat pathology associated with the occlusion of sebaceous gland ducts, and the resultant inflammation and infection in areas other than the eyelid (e.g. folliculitis).

C. Botulinum Toxin Compositions.

Treatment of severe or recurrent lesions associated with Chalazion or hordeola according to the methods of the present invention may be practiced by administering botulinum toxin at a biologic activity dose ranging from 0.25-50,000 mouse $LD_{50}$ units. Although one of ordinary skill evaluates dosing of the botulinum toxin based on several factors, including location and severity of the lesion, and other patient-specific factors, the proper dosing, depending on the composition and botulinum toxin immunotype, may be determined by using a regional denervation bioassay.

Preferably, a composition comprising botulinum toxin is administered along multiple sites along the lash base and over the meibomian glands, effectively bringing the neurotoxin or cytotoxin to the internal glandular structures. More preferably, the administration of botulinum toxin is accomplished by injection.

The methods of the present invention may be practiced with any one or more botulinum toxin immunotypes. The present invention also contemplates the use of compositions comprising botulinum toxin and sequestration agents such as albumin which are disclosed in U.S. patent application Ser. No. 10/740,755, filed on Dec. 22, 2003, which is incorporated herein by reference, in its entirety.

EXAMPLE

The following Example serves to further illustrate the present invention and is not to be construed as limiting its scope in any way.

Example 1

RK is a 44 year old man with a history of multiple chalazia and hordeola, having had to undergo at least four operations for the drainage of lesions. Recurrent infections resulted in chronic discharge and staining of glasses, and tearing with eyelid often becoming stuck together in early morning. Efforts at multiple antibiotics, warms compresses, lid soaps, expressions, and surgical drainage procedures failed to relieve the symptoms associated with the lesions. Efforts made to have Staphylococcal antigen desensitization were also not successful. Several injects of botulinum type A toxin resulted in 1. decreased size and number of lesions 2. reduced secretions and staining of eyeglasses and 3. decreased Staphylococcal infections along the eyelid margins.

We claim:

1. A method of treating chalazion, comprising the step of administering a therapeutically effective amount of a composition comprising botulinum toxin and a human serum albumin to a subject suffering from chalazion, wherein the composition reduces secretion from the meibomian glands and wherein the human serum albumin is present in an amount between 550 and 550,000 μg human serum albumin agent per 100 $LD_{50}$ units botulinum toxin.

2. The method of claim 1, wherein the composition is administered by injection into the eyelid or conjunctiva.

3. The method of claim 1, wherein there are at least two injection sites.

4. The method of claim 1, wherein the composition is administered at a dose between 0.5 and 50,000 mouse $LD_{50}$ units of botulinum toxin.

5. The method of claim 4, wherein the composition is administered by injection into the eyelid or conjunctiva.

6. The method of claim 1, wherein the botulinum toxin is immunotype A, B, C, D, E, F, or G.

7. The method of claim 6, wherein the composition is administered by injection into the eyelid or conjunctiva.

8. The method of claim 6, wherein the composition is administered at a dose between 0.5 and 50,000 mouse $LD_{50}$ units of botulinum toxin.

9. The method of claim 8, wherein the composition is administered by injection into the eyelid or conjunctiva.

10. A method of treating hordeolum, comprising the step of administering a therapeutically effective amount of a composition comprising botulinum toxin and a human serum albumin to a subject suffering from hordeolum, wherein the composition reduces secretion from the sebaceous glands and wherein the human serum albumin is present in an amount between 550 and 550,000 μg human serum albumin per 100 $LD_{50}$ units botulinum toxin.

11. The method of claim 10, wherein the botulinum toxin is immunotype A, B, C, D, E, F, or G.

12. The method of claim 10, wherein the composition is administered at a dose between 0.5 and 50,000 mouse $LD_{50}$ units of botulinum toxin.

13. The method of claim 10, wherein the composition is administered by injection into the eyelid or conjunctiva.

14. The method of claim 13, wherein there are at least two injection sites.

15. A method of treating a bacterial or fungal cutaneous infection, comprising the step of administering a composition comprising botulinum toxin and a human serum albumin to a subject suffering from a bacterial or fungal cutaneous infection in an amount sufficient to reduce secretion from meibomian or sebaceous glands, and reduce bacterial or fungal growth; wherein said administration is by injection and wherein the human serum albumin is present in an amount between 550 and 550,000 μg human serum albumin per 100 $LD_{50}$ units botulinum toxin.

16. The method of claim 15 wherein the cutaneous infection is caused by an organism selected from the group consisting of *Staphylococcus, Streptococcus,* and *Moraxella.*

17. The method of claim 15 wherein the cutaneous infection is in an area selected from the group consisting of eyelid, scalp, feet, groin, and armpit.

18. The method of claim 15, wherein the botulinum toxin is immunotype A, B, C, D, E, F, or G.

19. The method of claim 15, wherein the composition is administered at a dose between 0.5 and 50,000 mouse $LD_{50}$ units of botulinum toxin.

20. The method of claim 15, wherein there are at least two injection sites.

21. A method of reducing a sebaceous secretion on a body surface, comprising the step of administering a therapeutically effective amount of a composition comprising botulinum toxin and a human serum albumin to a subject in need of reduced sebaceous secretion, wherein the composition reduces sebaceous secretion; wherein said administration is by injection and wherein the human serum albumin is present in an amount between 550 and 550,000 μg human serum albumin per 100 $LD_{50}$ units botulinum toxin.

22. The method of claim 21, wherein the composition is administered to an area selected from the group consisting of eyelid, scalp, feet, external ear canal, groin, and armpit.

23. The method of claim 21, wherein the botulinum toxin is immunotype A, B, C, D, E, F, or G.

24. The method of claim 21, wherein the composition is administered at a dose between 0.5 and 50,000 mouse $LD_{50}$ units of botulinum toxin.

25. The method of claim 21, wherein there are at least two injection sites.

* * * * *